United States Patent
King et al.

(10) Patent No.: US 6,993,955 B1
(45) Date of Patent: Feb. 7, 2006

(54) GAS SENSORS

(75) Inventors: Charles Edmund King, Oxfordshire (GB); Peter John Smith, Oxfordshire (GB)

(73) Assignee: City Technology Limited, Partsmouth (GB)

( * ) Notice: Subject to any disclaimer, the term of this patent is extended or adjusted under 35 U.S.C. 154(b) by 57 days.

(21) Appl. No.: 10/130,764

(22) PCT Filed: Nov. 23, 2000

(86) PCT No.: PCT/GB00/04467

§ 371 (c)(1), (2), (4) Date: Aug. 20, 2002

(87) PCT Pub. No.: WO01/38867

PCT Pub. Date: May 31, 2001

(30) Foreign Application Priority Data

Nov. 23, 1999 (GB) .................................. 9927689

(51) Int. Cl.
*G01N 31/10* (2006.01)
*G01N 27/04* (2006.01)

(52) U.S. Cl. .................... 73/31.06; 73/23.31; 338/34; 422/90

(58) Field of Classification Search .............. 73/31.06, 73/23.31; 338/34; 422/90
See application file for complete search history.

(56) References Cited

U.S. PATENT DOCUMENTS

| | | | |
|---|---|---|---|
| 3,886,785 A | 6/1975 | Stadler et al. | |
| 4,569,826 A * | 2/1986 | Shiratori et al. | 422/90 |
| 4,935,289 A * | 6/1990 | Kikuchi et al. | 428/209 |
| 5,633,081 A | 5/1997 | Clough et al. | |
| 5,736,104 A * | 4/1998 | Oh et al. | 422/96 |
| 5,811,662 A * | 9/1998 | Williams et al. | 73/31.06 |
| 5,840,255 A | 11/1998 | Kappel et al. | |
| 5,918,261 A | 6/1999 | Williams et al. | |
| 6,046,054 A * | 4/2000 | McGeehin et al. | 436/121 |
| 6,069,013 A * | 5/2000 | Plog et al. | 436/113 |

FOREIGN PATENT DOCUMENTS

JP   05045138 A * 2/1993
WO   WO 99/25474   5/1999

OTHER PUBLICATIONS

Morrison, S. Roy "Semiconductor Gas Sensors", Sensors and Actuators vol. 2, 1982 no month, pp. 329-341.*
Shimizu et al. "Basic aspects and challenges of semiconductor gas sensors", MRS Bulletin, vo. 24, Jun. 1999, pp. 18-24.*
Kawahara, A. et al. "Gas-Sensing Properties of Semiconductor Heterolayers Fabricated by a Slide-Off Printing Method" Technical Digest of the International Meeting on Chemical Sensors, Jun. 1998, pp. 374-376.*
Feng, C. D. et al. "Effect of Gas Diffusion Process on Sensing Properties of SnO2 Thin Film Sensors in a SiO2/SnO2 layer-built structure fabricated by sol-cel process" Journal of the Electrochemical Society, Jan. 1994, vol. 141, p. 220-25.*

* cited by examiner

Primary Examiner—Michael Cygan

(57) ABSTRACT

Semiconductor gas sensors with improved selectivity to target gases are provided by having a semiconductor gas-sensing layer and a layer thereon of microporous ceramic oxide having catalytic activity.

13 Claims, 6 Drawing Sheets

GAS SENSORS

Figure 1:
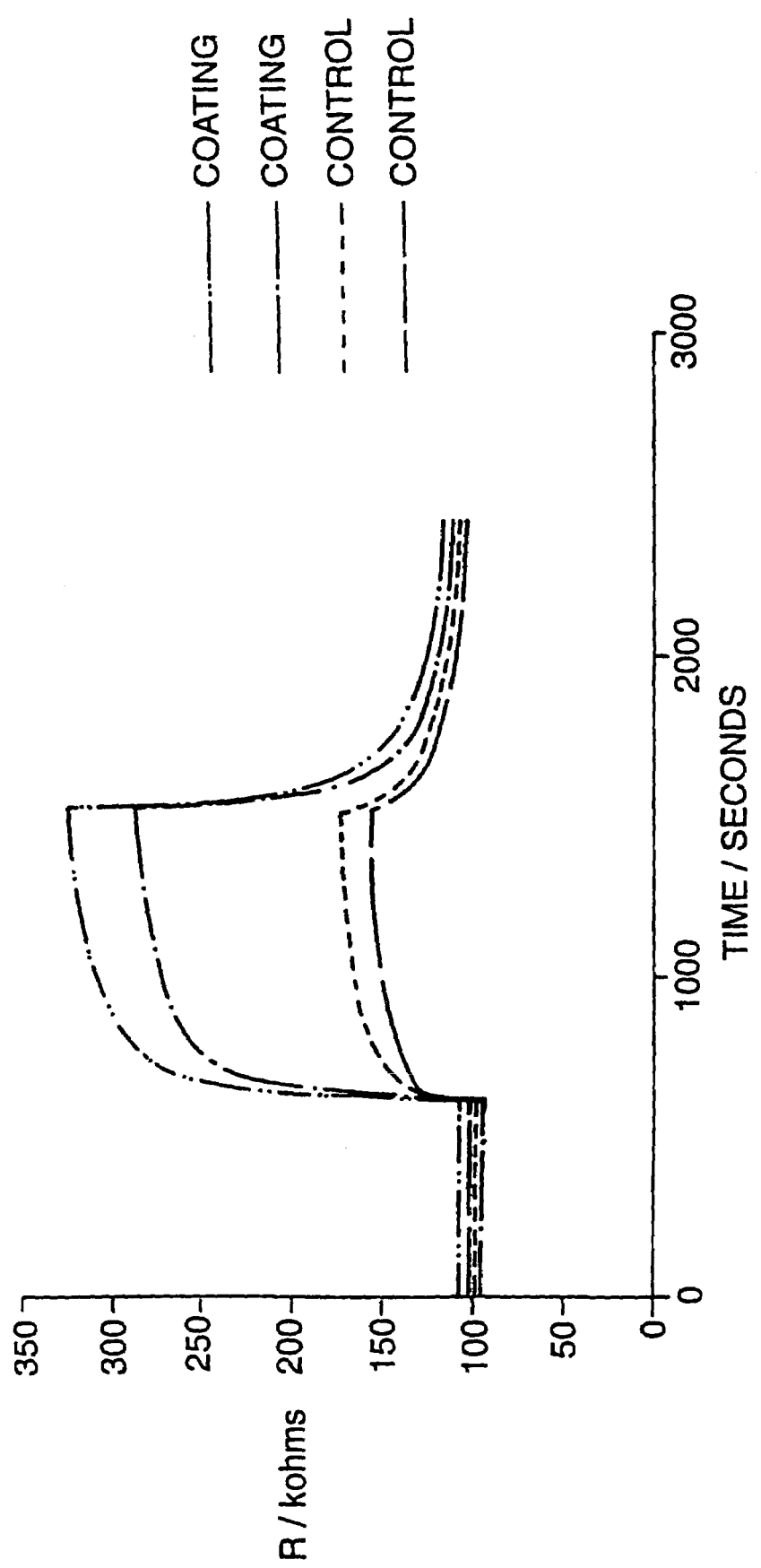

Amongst the many technical challenges facing manufacturers of semiconductor sensors/detectors is the need to avoid false alarms. The common cause of false alarms is the presence in the vicinity of the detector of a gas (so-called interference gas) to which the detector responds in a way similar to that for the target gas. To improve the specificity of the detector, one common approach for gas detectors based on semiconductor sensors is to employ a filter material such as activated carbon. Protection against the more common interference gases is achieved provided their concentration is not too high so as to overwhelm the filter. However, this approach suffers from a number of disadvantages, such as a finite absorption capacity, an increased response time and a specificity which may not suit all sensors: carbon blocks hydrocarbons, alcohols and hexamethyldisiloxane (HMDS) but is less adsorbent to ammonia, carbon monoxide, hydrogen and methane.

Other approaches to provide selectivity have been cited in the literature. One such approach is to use sophisticated two-temperature operation modes, as described in U.S. Pat. No. 5,517,182. The sensor surface is purged at the at the higher temperature, while differentiation between the various gases is achieved at the lower temperature by virtue of the faster rate of response of the smaller molecules, such as CO. Another approach is to dope the semiconductor with another oxide so as to enhance its catalytic activity towards the target gas while suppressing it towards other gases (1, 2). This approach requires that the surface electrical properties of the semiconductor are not adversely affected. Enrichment of the surface of the semiconductor grains with a catalyst such as platinum or palladium is still another approach (1, 2). Increased sensitisation has been reported but as with all technologies revolving around noble metal catalysts, poisoning of the noble metal is a potential weakness.

A third approach is to use a coating over the sensor to promote combustion of the heavier gases, which in many cases constitute the interferent gases, prior to reaching the "sensing" layer (2,3). DE19708770 describes the use of a catalytic pre-oxidation filter, comprised of a thick porous layer of Ga2O3 above a thin-film Ga2O3 gas sensor, for detecting methane. The presence of the pre-oxidation filter is claimed to eliminate cross-sensitivities to ethanol and to other organic interferent gases. EP0280540 describes the use of an outer catalyst layer fabricated of either conductive or non-conductive material to promote combustion of interferent gases. The conductive material is tin oxide impregnated with Pt or Pd and requires a porous glass layer positioned between the sensing material and the filter layer. The non-conductive material is Pt- or Pd-doped alumina and does not require the porous glass layer. In these examples, increased specificity is achieved primarily by reducing or suppressing the response to the interferent gas through accelerated combustion while the response to the target gas remains unaffected. Elsewhere (4, 5), the use of coatings have been shown to provide a significant enhancement in sensitivity to simple mobile gases, such as hydrogen and carbon monoxide. Here the coatings which are applied in a dense manner, act to slow down the diffusion of oxygen to the sensing layer while the inward fluxes of the faster diffusing hydrogen and carbon monoxide are relatively unchanged. The resulting low oxygen partial pressure in the interior regions is responsible for the higher sensitivities observed for hydrogen and carbon monoxide. Accordingly, the teaching in the prior art suggests that coatings are beneficial in providing selectivity where the target gas in a small molecule and the interferent gas is a larger molecule.

We have now found that if we deposit a microporous coating of a ceramic oxide powder having catalytic activity onto the semiconductor layer, amplification of the response to the heavier gas is possible. We have also found in certain cases that the coating suppresses all gas responses but more so, the responses to the lighter gases. The microporous layer is in intimate contact with the underlying semiconductor layer and, therefore, becomes "hot" on powering up the sensor. As such, its catalytic activity is increased. The ceramic powder does not contain any precious metal such as Pt or Pd and thereby, is resistant to a loss in activity through poisoning.

The ceramic material is oxide in nature and is of the form AO, ABO or ABCO where the cations A, B, C are from the First Transition Series of elements and/or may also come from one of the following: La, Ce, Pr, Zr, Mo, W, Al, Si, Sn, Pb and Bi. The approach avoids altering the electrical characteristics of the semiconductor, as the sensing layer/electrode geometry is chosen so that the coating material is outside the area interrogated by the field lines from the electrodes (6). The approach may be used be as the sole filtering method or in association with a carbon filter. Increased specificity is achieved through amplification of the response to the target gas without changing the response to the interferent gas (or in some cases suppressing it), or, through a reduced suppression of the response to the target gas compared to those of the interferent gases.

The choice of the ceramic powder used in the coating will depend on the particular target gas. Thus, one can increase the sensitivity to a target gas through careful selection of the coating material. For example if the target gas is propane—a requirement in fuel cells or where vehicles/appliances are powered by liquid petroleum gas (LPG)—the use of NiO, Ga2O3 or (Fe, Cr)2O3 coatings would be recommended to amplify the sensor response over the likely contaminants, hydrogen and CO. Alternatively, if the application is to detect CO in a domestic environment, the use of CuCr2O4 or CrTiMinO coatings is preferable.

The microporous layer may be of the same material as the sensing layer itself. However, as this amounts effectively to increasing the thickness of the sensing layer, significant changes in the relative sensitivities do not occur. Adhesion between the coating and the underlying sensing oxide can be problematic if there are large differences in thermal expansion, with spallation of the coating occurring. Methods familiar to those skilled in the art such as additions of thermal expansion modifiers, using lower coating thicknesses and firing to lower temperatures can be used to minimise the build up of thermal stresses and, thus, improve adhesion.

EXAMPLES

In the Examples that follow, the materials investigated are described in Table 1, while the results highlighting the degree of selectivity are described in Table 2 and Table 3.

A semiconductor sensor based on the Cr—Ti—O system as the sensing oxide, as described in WO 95/00836, was used in all the examples. The Cr—Ti—O system is a p-type material and undergoes an increase in electrical resistance in the presence of reducing gases. The sensor build is described in various Capteur Sensors' product data sheets for the G series of sensors for detecting carbon monoxide, for example GS07 and GL07 data sheets. During assembly of the sensors, the semiconductor 90 micron Cr—Ti—O layers were coated with the materials shown in Table 1 by screen printing inks comprised of the coating materials and a terpiniol vehicle system supplied by ESL. The solids loading in the coating inks varied from 66 wt % to 50 wt %, depending on the surface area and particle size of the oxide used. Unfired print thickness for each of the coatings are also given in Table 1. The resulting composite structure was co-fired to 800° C. prior to assembling into the standard build. As described in the product data sheet, the sensors were powered up alongside standard sensors to approx. 400° C. such that the electrical resistances were 100 kohms in 50% RH clean air. Following stabilisation for a period of 20 minutes, the sensors were then exposed to various test gases for 20 minutes with cleaning air steps in between. The test gases used were air—400 ppm CO, air—200 pppm propane, air—400 ppm propane, and air—400 ppm hydrogen. The benefit of improved specificity to propane through amplification of the propane response is shown in Table 2.

Comparison should be made with the control (i.e. no coating) and with the CTO-coated sensor.

\* Oxide mixed with Ga2O3 in the ratio of 4 parts: 1 art of Ga2O3 and mixture homogenised by sieving through a 38 micron mesh \*\* Oxide mixed with Ga2O3 in the ratio of 1 parts: 1 part of Ga2O3 and mixture homogenised by sieving through a 38 micron mesh \*\*\* Oxide mixed with low-melting lead glass in the ratio of 2 parts to 1 part of lead glass and homogenised by sieving through a 38 micron mesh.

TABLE 2

Results Showing Amplification Effects of Coatings on Responses to Propane

| Coating | $R_{400ppmP}/R_{400ppmCO}$ ^ | $R_{400ppmP}/R_{400ppmH}$ ^^ |
|---|---|---|
| $Cr_2O_3$ | .75–0.95 | 1.05 |
| $Fe_{1.2}Cr_{0.8}O_3$ | .75–0.90 | |
| $Mn_2O_3$ | .65 | .84 |
| $SnO_2$-0.7 wt % $Sb_2O_3$ | .64 | .86 |
| NiO* | 1.13 | 1.18 |
| $SiO_2$* | .76 | .85 |
| $Co(Cr, Al)_2O_4$** | .71 | 1.01 |
| $CoTi_2O_4$** | .58 | .88 |
| $WO_3$ | .89 | .99 |
| $Al_2O_3$ | .59 | .80 |
| Zeolite 4A*** | .85 | 1.06 |
| Cr—Ti—O | .61 | .85 |
| Control - no coating | .54 | .73 |

^ The ratio of the sensor response in 400 ppm propane to that in 400 ppm CO
^^ The ratio of the sensor response in 400 ppm propane to that in 400 ppm hydrogen

TABLE 1

Oxide Materials used as Coatings

| Coating Material | Supplier | Powder Details | Dry Print Thickness (microns) |
|---|---|---|---|
| $Cr_2O_3$ | Johnson Matthey | $D_{50}$ = 0.2 micron, 7 $m^2$/g | 100 microns |
| $Fe_{1.2}Cr_{0.8}O_3$ | Johnson Matthey | $D_{50}$ = 0.6 micron, 12 $m^2$/g | 100 microns |
| $Mn_2O_3$ | Sigma-Aldrich Company Ltd | –325 mesh | 100 microns |
| SnO2-0.7 wt % Sb2O3 | Sigma-Aldrich Company Ltd | –325 mesh, 8 $m^2$/g | 50 microns |
| NiO* | Sigma-Aldrich Company Ltd | <10 microns | 60 microns |
| $SiO_2$* | Sigma-Aldrich Company Ltd | –325 mesh | 70 microns |
| $CuCr_2O_4$-6% BaO | Strem Chemicals Ltd | 45–50 $m^2$/g | 100 microns |
| $CuCr_2O_4$** | Johnson Matthey | $D_{50}$ = 1.1 micron, 6 $m^2$/g | 100 microns |
| Co(Cr, Al)2O4 | Johnson Matthey | $D_{50}$ = 1.2 microns, 11 $m^2$/g | 100 microns |
| CoTi2O4 | Johnson Matthey | $D_{50}$ = 1.7 microns, 7 $m^2$/g | 100 microns |
| $WO_3$ | Capteur Sensors and Analysers Ltd | $D_{50}$ = 0.8 microns, 2 $m^2$/g | 60 microns |
| Zeolite 4A*** | The Smart Chemical Company | $D_{50}$ = 5 microns | 15 microns |
| Cr—Ti—Mn—O | Capteur Sensors and Analysers Ltd | $D_{50}$ = 0.8 microns | 100 microns |
| Cr—Ti—O | Capteur Sensors and Analysers Ltd | $D_{50}$ = 0.8 microns, 5 $m^2$/g | 100 microns |

*Oxide mixed with Cr2O3 in the ratio of 4 parts: 1 part of Cr2O3 and mixture homogenised by sieving through a 38 micron mesh
**Oxide mixed with Cr2O3 in the ratio of 1 parts: 1 part of Cr2O3 and mixture homogenised by sieving through a 38 micron mesh
***Oxide mixed with low-melting lead glass in the ratio of 2 parts to 1 part of lead glass and homogenised by sieving through a 38 micron mesh.

~The ratio of the sensor response in 400 ppm propane to that in 400 ppm CO

~~The ratio of the sensor response in 400 ppm propane to that in 400 ppm hydrogen

TABLE 3

Results Showing Effects of Coatings on Selectivity to Carbon Monoxide

| Coating | $R_{400ppmCO}/R_{400ppmP}$ $ | $R_{400ppmCO}/R_{400ppmH}$ $$ |
|---|---|---|
| CuCr$_2$O$_4$ | 2.38 | 1.69 |
| Cr—Ti—Mn—O | 2.56 | 1.69 |
| Control - no coating | 1.85 | 1.35 |

$The ratio of the sensor response in 400 ppm CO to that in 400 ppm propane
$$The ratio of the sensor response in 400 ppm CO to that in 400 ppm hydrogen Example 1

(FIG. 1)

On exposure to 200 ppm propane at 50% relative humidity, the standard sensors (i.e. no coating) show resistance values of 150–170 kohms, while the 100 micron-thick-$Cr_2O_3$-coated sensors showed enhanced sensitivities with resistance increases to 290 and 330 kohms being observed. This serves to highlight the amplifying effect of $Cr_2O_3$ on the response to propane.

Example 2

(FIG. 2)

Figure 2:
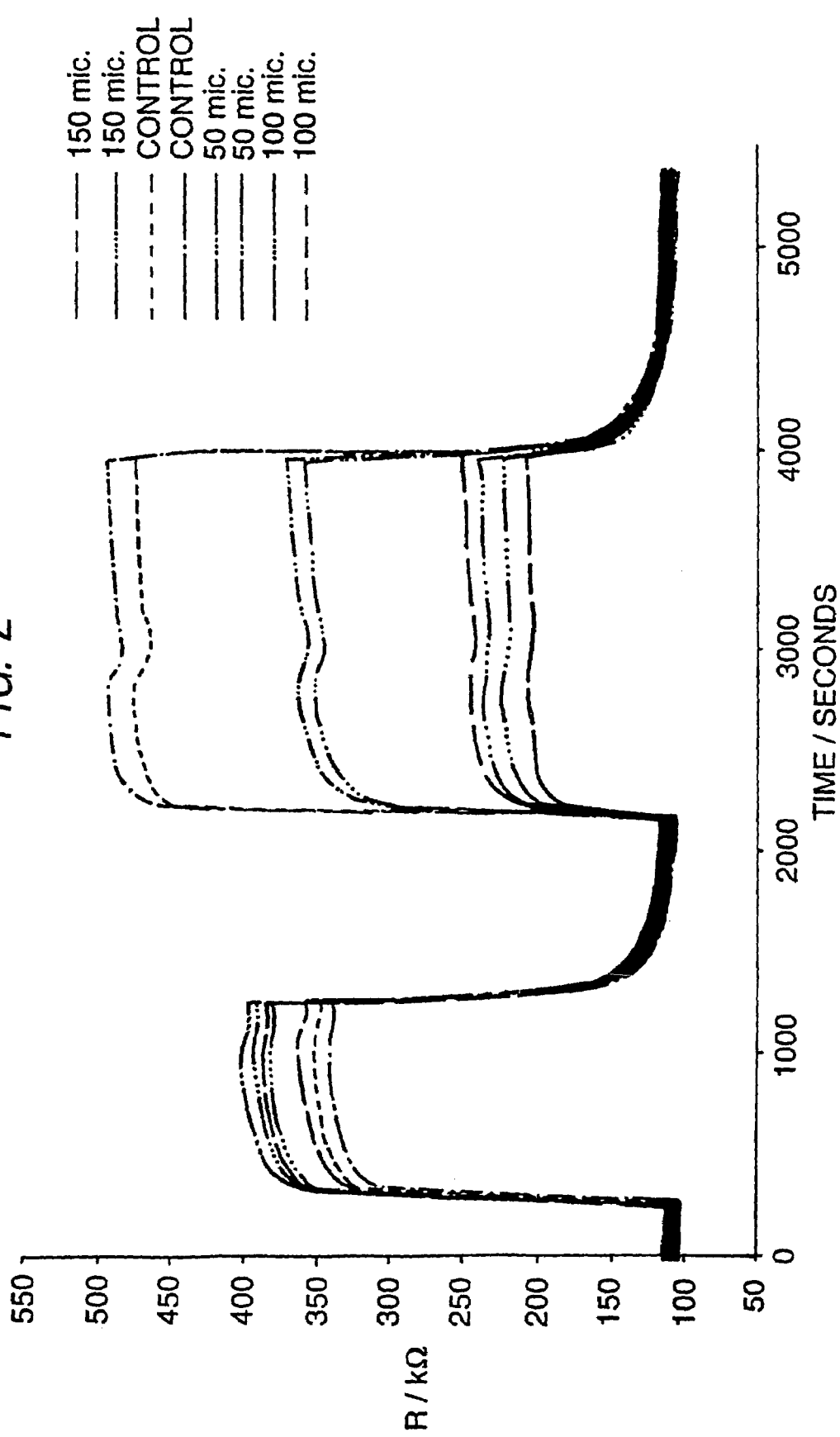
Figure 3:
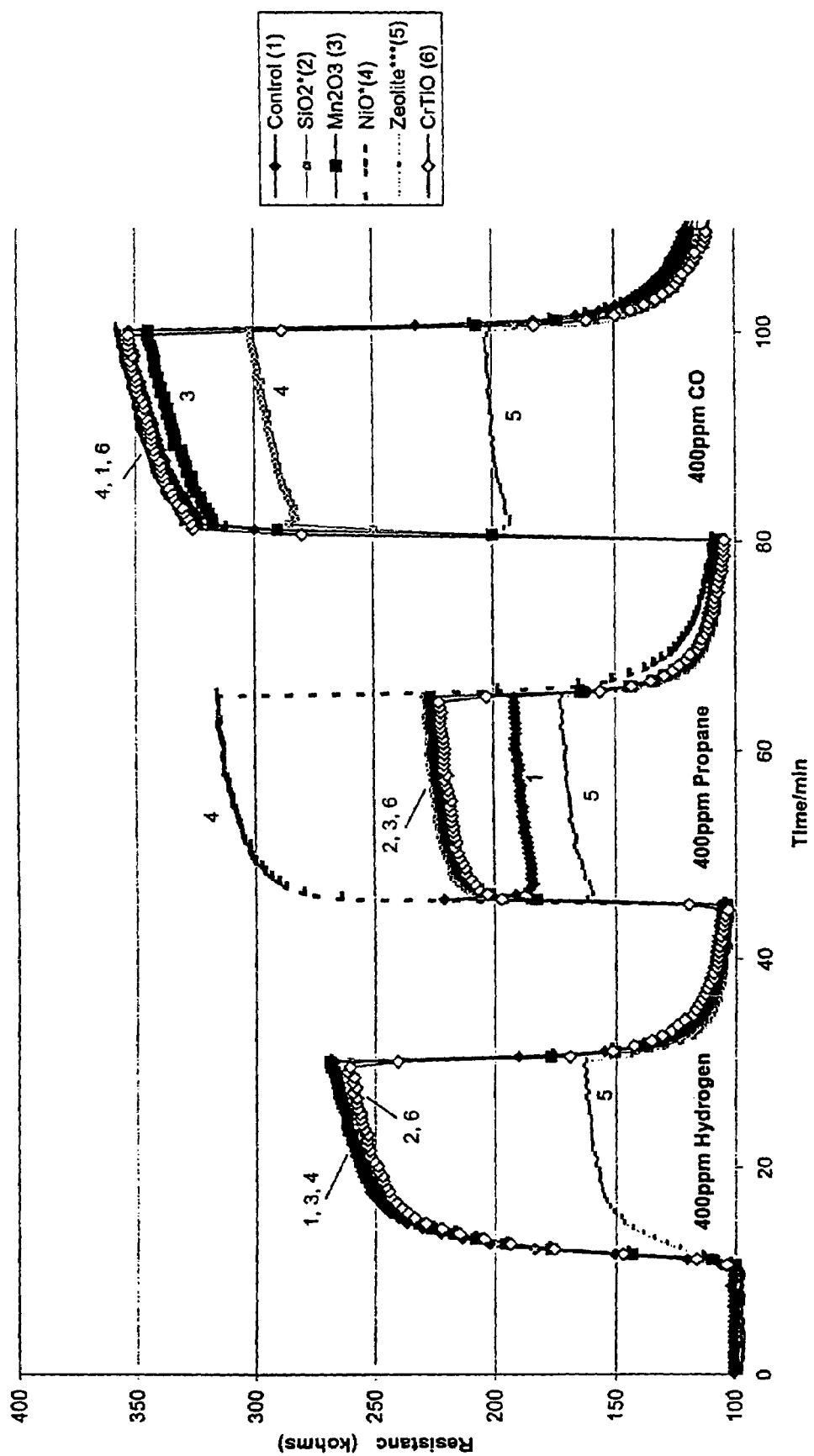
Figure 4:
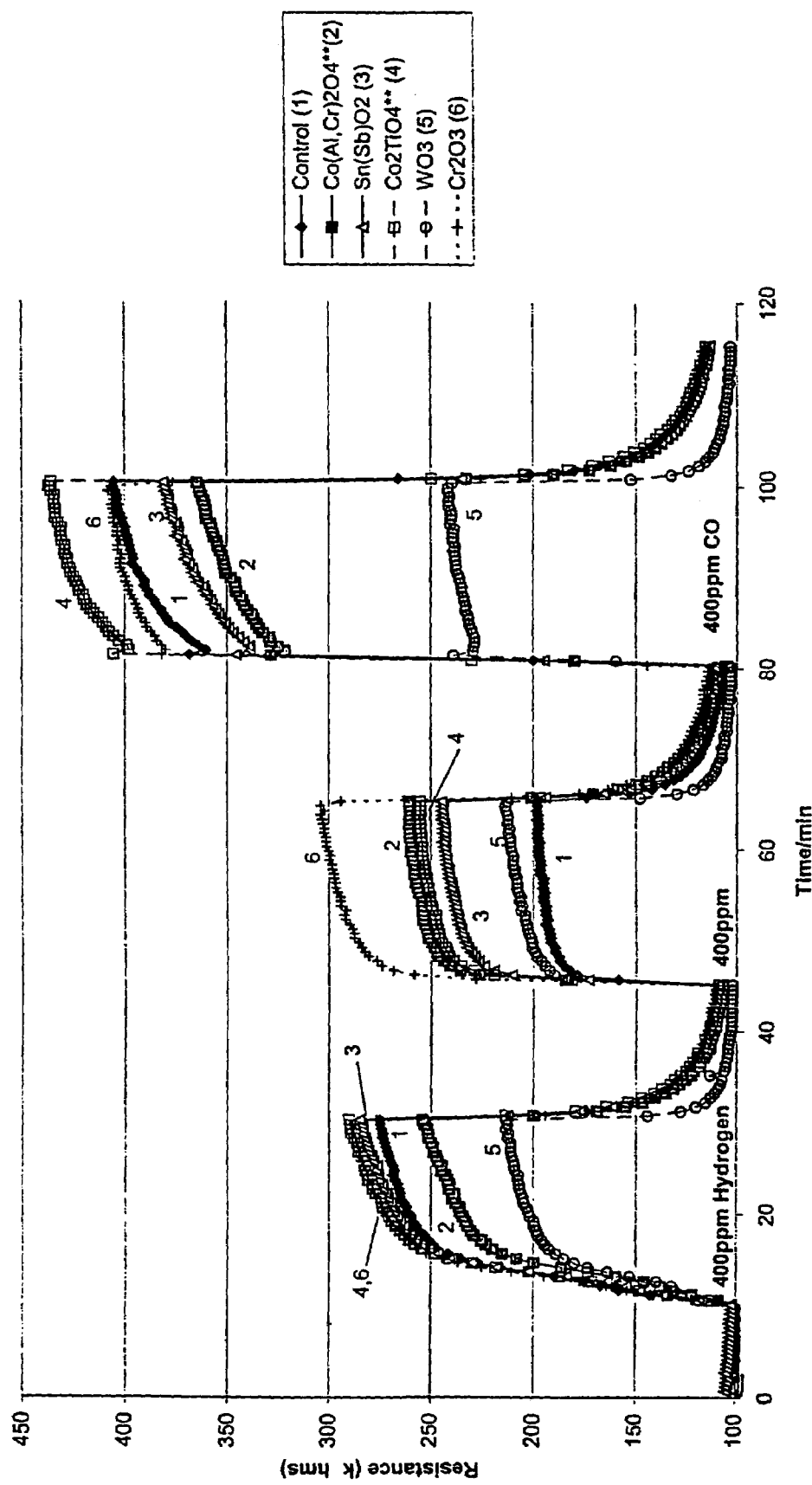
Figure 5:
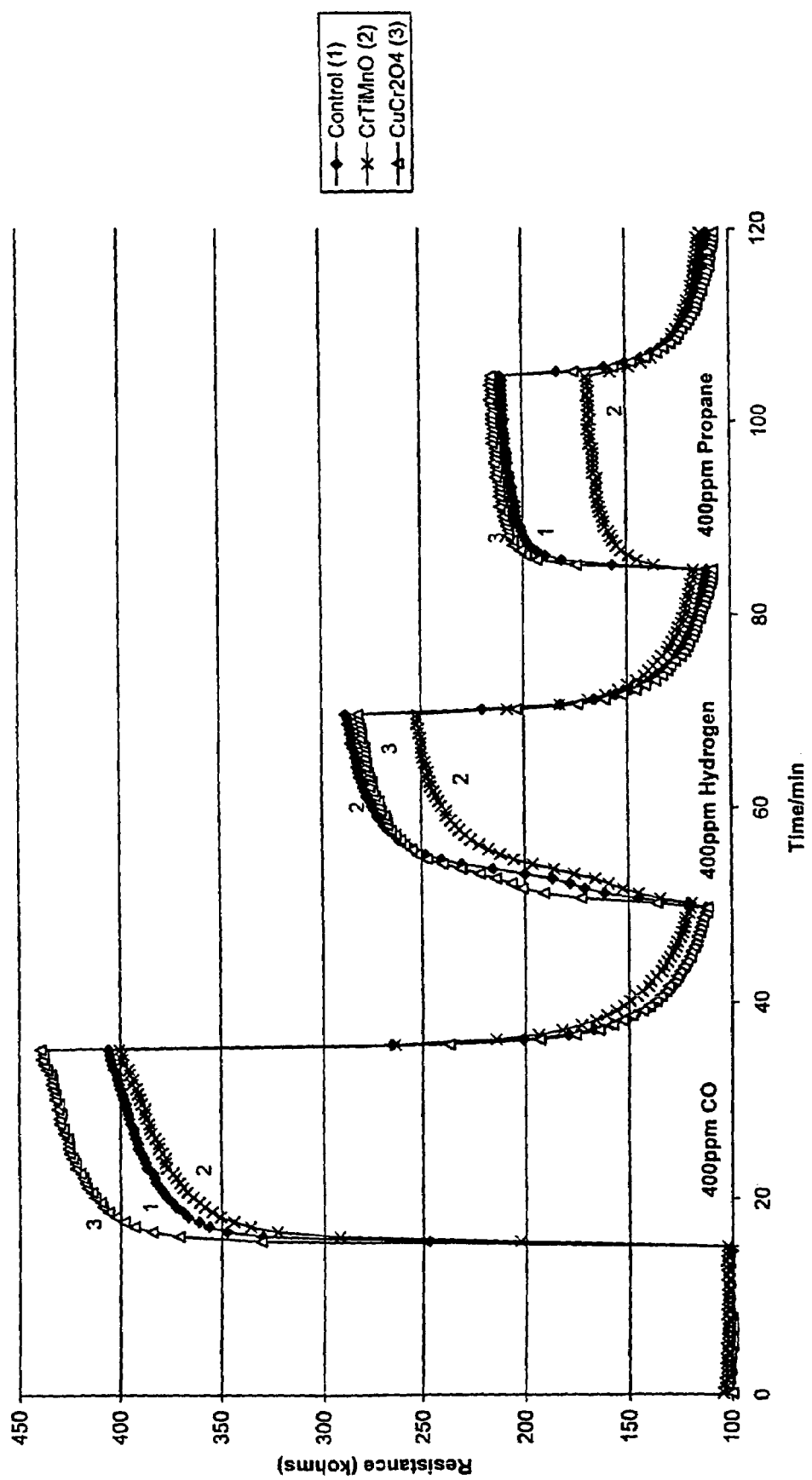
Figure 6:
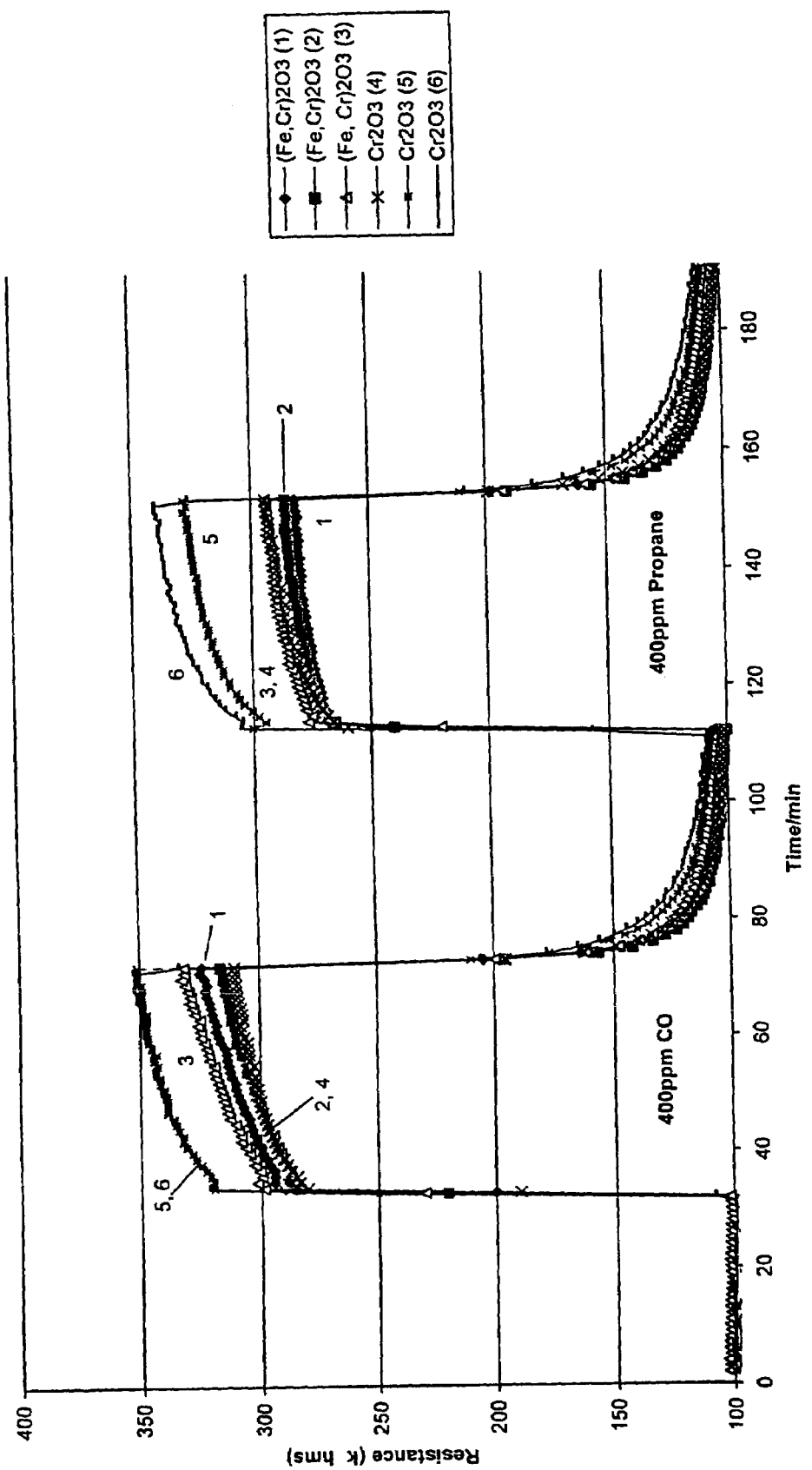

As in Example 1, except in this case, $Cr_2O_3$ coatings of unfired print thicknesses of 50 and 150 microns were also investigated. Following stabilisation in clean air, the sequence of gas steps was 20 minutes in 400 ppm CO, 15 minutes in clean air, 30 minutes in 36 ppm ethanol, followed by 20 minutes in clean air. All gas steps were carried out at 50% RH. As shown in FIG. 2, the coated and uncoated sensors have similar responses to CO but the coating thickness affects the response to ethanol. The standard sensors give a response of 460–480 kohms to 36 ppm ethanol. Applying a coating of 50 microns thick reduces the response by 120–140 kohms or by 25–30%. For increased thicknesses of 100 and 150 microns, greater reductions in response by 250–280 kohms or by 50–60% are observed. This example serves to highlight the reduced cross-sensitivity of the $Cr_2O_3$-coated Propane/CO sensors to ethanol.

Example 3

(FIG. 3)

As in Example 1, but using sensors coated with a range of different ceramic materials, as described in Table 1. The sensors were exposed to the test regime: 10 minutes air, 20 minutes 400 ppm Hydrogen, 15 minutes air, 20 minutes 400 ppm Propane, 15 minutes air, 20 minutes 400 ppm CO followed by 15 minutes in air. The coatings applied have the effect of amplifying the response to propane compared to the interferent gases, hydrogen and CO. The sole exception is the zeolite/glass coating which suppresses the responses to hydrogen and to carbon monoxide more strongly than the response to propane.

Example 4

(FIG. 4)

As for Example 3 but using different coating materials (Table 1), showing the effect of amplifying the sensor response to propane.

Example 5

(FIG. 5)

In this Example, two coating materials (as described in Table 1) provide selectivity towards carbon monoxide relative to hydrogen and to propane. The test regime used was: 15 minutes air, 400 pm CO, 15 minutes air, 20 minutes 400 ppm hydrogen, 15 minutes air, 20 minutes 400 pm propane, 15 minutes air. The $CuCr_2O_4$ coating provides selectivity through amplification of the response to carbon monoxide unlike the CrTiMnO coating which does not alter the CO response but suppresses the responses to hydrogen and propane.

Example 6

(FIG. 6)

A comparison is made between sensors coated with 100 micron-thick $Cr_2O_3$ and (Fe, $Cr)_2O_3$ in this Example. The test regime used was 30 minutes air, 40 minutes in 400 ppm CO, 40 minutes air, 40 minutes 400 ppm propane, 40 minutes air. Both coating materials (Table 1) amplify the propane response by similar amounts relative to the CO response.

REFERENCES

1. R. Morrison, Sensors and Actuators (1982), 2, p 329–341.
2. Y. Shimizu and M. Egashira, Materials Research Society Bulletin (1999), p 18–24.
3. N. Yamazoe, Y. Muto and T. Seiyama (1984), Hyomen Kagaku, 5, p 241.
4. C. Feng, Y. Shimizu and M. Egashira, J. Electrochem. Soc. (1994), 141, p 220.
5. A. Kawahara et al, Technical digest of the 7$^{th}$ international Meeting on Chemical Sensors (International Academic Publishers, Beijing, 1998), p 364.
6. D. Williams et al, U.S. Pat. No. 0,0591,826,1

What is claimed is:

1. A gas sensor comprising:
   a semiconductor gas-sensing layer;
   a filter layer of microporous, precious metal free ceramic oxide having a catalytic activity coated on the gas-sensing layer, the microporous ceramic oxide being of a different material than the gas-sensing layer, the ceramic oxide being an oxide of one or more first order transition elements and/or one or more of La, Ce, Pr, Zr, Mo, W, Al, Si, Sn, Pb, and Bi; and
   at least two electrodes in contact with the gas-sensing layer for monitoring the resistance of the gas-sensing layer.

2. A gas sensor according to claim 1 wherein the filter layer is adapted to amplify the response of the sensor to a target gas.

3. A gas sensor according to claim 1 wherein the ceramic oxide is $Cr_2O_3$.

4. A gas sensor according to claim 3 wherein the semiconductor gas-sensing layer is chromium titanate.

5. A gas sensor according to claim 3 further comprising a carbon filter.

6. A gas sensor according to claim 1 wherein the semiconductor gas-sensing layer is chromium titanate.

7. A gas sensor according to claim 1 further comprising a carbon filter.

8. A gas sensor according to claim 1, wherein the microporous, precious metal free ceramic oxide layer is screen printed on the gas-sensing layer.

9. A gas sensor according to claim 1 wherein the filter layer has an unfired thickness of between 15 microns and 150 microns inclusive.

10. A method of manufacturing a gas sensor comprising the steps of: screen-printing a semiconductor layer onto a substrate; coating a filter layer of microporous, precious metal free ceramic oxide having a catalytic activity onto the semiconductor gas-sensing layer, the microporous oxide filter layer being of different material than the gas-sensing layer;

co-firing the semiconductor and ceramic oxide layer; and providing at least two electrodes in contact with the gas-sensing layer for monitoring the resistance of the gas-sensing layer.

11. A method according to claim 10 wherein the ceramic oxide is screen printed with an ink comprising a ceramic oxide powder dispersed in a liquid vehicle.

12. A method according to claim 11 wherein the powder has a surface area of 5 to 50 $m^2/g$ and a particle size of 0.001 to 50 microns.

13. A method according to claim 10, wherein the coating step comprises screen printing.

* * * * *